United States Patent [19]

Lahav et al.

[11] Patent Number: 5,047,535
[45] Date of Patent: Sep. 10, 1991

[54] N-HETEROCYCLIC AMPHIPHILIC AMIDES

[75] Inventors: Meir Lahav; Leslie Leiserowitz, both of Rehovot; Jacob Sagiv, Ness Ziona; Ronit Popovitz-Biro, Rehovot, all of Israel; Karlheinz Hill, Bad Berneck, Fed. Rep. of Germany; Ehud Landau, Rehovot, Israel

[73] Assignee: Yeda Research and Development Company Limited, Rehovot, Israel

[21] Appl. No.: 81,769

[22] Filed: Aug. 5, 1987

[30] Foreign Application Priority Data

Aug. 5, 1986 [IL] Israel .................................... 79624

[51] Int. Cl.$^5$ ........................... C07F 9/06; C07F 9/28; C07D 249/12; C07D 233/54
[52] U.S. Cl. ...................................... 546/22; 546/265; 546/335; 546/336; 546/337; 546/267; 546/291; 546/309
[58] Field of Search ................ 546/291, 267, 22, 265, 546/335, 336, 337; 428/435; 564/209, 215, 182, 166, 167, 109, 153, 157, 158, 159, 153, 157, 158, 159; 560/21, 22, 41, 104, 105; 562/434, 450, 494, 496; 558/170

[56] References Cited

U.S. PATENT DOCUMENTS

| 3,541,135 | 11/1970 | Johl et al. | 546/291 |
| 4,126,628 | 11/1978 | Paquet | 546/291 |
| 4,536,450 | 8/1985 | Garito | 428/435 |

FOREIGN PATENT DOCUMENTS

| 1554477 | 12/1968 | France | 546/291 |
| 2192795 | 2/1974 | France | 546/291 |
| 751524 | 6/1956 | United Kingdom | 546/291 |
| 2028810 | 11/1978 | United Kingdom | 546/291 |

OTHER PUBLICATIONS

Journal of the American Chemical Society, vol. 110, Apr. 13, 1988, pp. 2672-2674, Popovitz-Biro et al., *A New Class of Stable Head-To-Tail (Z-type) Langmuir Blodgett Films, A Second Harmonic Generation Study.*
Chemical Abstracts, vol. 84, No. 19, May 10, 1976, p. 89, Abstract No. 130817s, Kashima et al., *Inhibition of Bacteriophages of Amino Acid Producing Bacteria by N-Acylamino Acids*, & 9th Collective Index, 18614CS, 6-[1-oxohexadecy) amino] hexanoic acid.
Chemical Abstracts, vol. 92, No. 1, Jan. 7, 1980, p. 198, Abstract No. 1977k, Zaslavskii et al., *Action of Surface-Active Substances on Biological Membranes* & 10th Collective Index, 35515Cs, 8-[(1-oxododecyl) amino] actanoic acid, monosodium salt.
Chemical Abstracts, vol. 90, No. 10, Mar. 5, 1979, p. 39, Abstract No. 80854c, Rasteniene, *Study of the Effect of the Intravenous Injection of N-acyl-e-aminocaproic Acid Derivatives On the Concentration of Lactic Acid in Rabbit Blood*, & 10th Collective Index 25345CS, 6-[(1-oxoundecyl)amino] hexanoic acid . . . hexanoic acid.
Chemical Abstracts, vol. 93, No. 21, Nov. 24, 1980, p. 238, Abstract No. 199583r, Paquet, *Preparation of Some Long-Chain N-acyl Derivative of Essential Amino Acids for Nutritional Studies.*
Chemical Abstracts, vol. 103, No. 11, Sep. 16, 1985, p. 5, Abstract No. 88280v, Laporte et al., *Reaction of Alpha, w-dicarboxy Polyamides in the Melt: Synthesis of a Model, Use of N-Trifluoroacetylation in NMR and GPC Studies* & 11th Collective Index, 69647CS, 11-[1-oxododecyl)amino]undecanoic acid.
Chemical Abstracts, vol. 104, No. 7, Feb. 17, 1986, p. 92, Abstract No. 52453k, Sheth et al., Effect of Structure on Surfactance of Amide Intermediate Linked Carboxylates & 11th Collective Index, 32474CS, 6-[-1-oxododecyl)amino]hexanoic acid, monosodium salt.
Nature, vol. 328, Jul. 2, 1987, pp. 63-66, Wolf et al., *Elucidation of the Two-Dimensional Structure of an alpha-amino acid surfactant monolayer on water using synchrotron X-ray diffraction.*
Journal of the American Chemical Society, vol. 101, No. 14, Jul. 4, 1979, pp. 3920-3927, Molinari et al., *Polymer-supported phase-transfer catalysts, High Catalytic Activity of Ammonium and Phosphonium Quaternary Salts Bonded to a Polystyrene Matrix.*

Primary Examiner—Mary C. Caleb
Assistant Examiner—Robert C. Whittenbaugh
Attorney, Agent, or Firm—Browdy and Neimark

[57] ABSTRACT

The invention relates to novel compounds which are suited for the production of multilayer films which have piezoelectric, and pyroelectric properties, and which provide second harmonic generation. The novel compounds are amphiphilic and it is possible to prepare from same polar single-layer and multi-layer films by depositing them on a substrate. When such substrate is a solid support, polar Z-type Langmuir-Blodgett films are obtained. Upon compression of films of such compounds, at an air/water interface, stable Langmuir monolayers are formed.

1 Claim, No Drawings

N-HETEROCYCLIC AMPHIPHILIC AMIDES

FIELD OF THE INVENTION

The invention relates to novel amphiphilic compounds and to polar single- or multilayer films prepared from these on a suitable solid substrate. Upon compression at a suitable air/water interface, stable Langmuir monolayers are formed. When such monolayers are deposited on a solid support, polar Z type Langmuir-Blodgett films are obtained.

BACKGROUND OF THE INVENTION

Many amphiphilic molecules composed of an hydrophobic tail and an hydrophilic head group form Langmuir monolayer films upon compression at an air/water interface. It has been reported that such layers can be deposited onto a solid support such as glass, gold, aluminium, etc, to form non polar Y-type Langmuir-Blodgett films.

SUMMARY OF THE INVENTION

The invention relates to compounds suitable for the formation of polar mono- or multiple-layer films. When deposited on a suitable solid support such as glass, gold, aluminium etc., the amphilphilic molecules of such compounds are compressed at the interface and form such films. The films are stable and have interesting piezoelectric, pyroelectric properties and result in second harmonic generation.

The amphiphilic molecules have a hydrophilic moiety at one end, a chain comprising at least one, and preferably two amido linkages, said hydrophobic chain comprising at least about 14 carbon atoms, the terminal methyl group being substituted by any of wide variety of substituents, such as p-nitroaniline, p-nitrocinnamic acid, styrene, a merocyanine group etc.

The compounds according to the invention can have a wide scope of terminal substituents, typical compounds of the present invention are of the formula $$R-(CH_2)_n-CONH-(CH_2)_m-(CONH)_p-(CH_2)_q-R_1$$

where R designates —CH$_3$, —CH$_2$Hal, —CH=CH—φ, —NH—φ—NO$_2$,

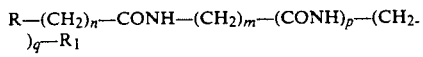

where R designates —OH, —COOH, —NH$_2$, —CONH$_2$, —PO$_3$=,

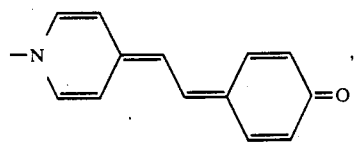

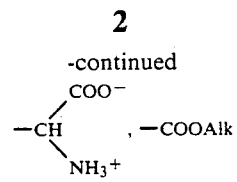

where Hal designates a halogen atom, Alk designates an alkali metal atom, the sum of n, m and q is 14, and p is zero or one, and where there may be more than 2 alkylamido entities. When compressed at an air/water interface they form stable Langmuir type monolayers. These on transfer to a solid support such as glass, aluminium, or glass coated with a thin organic or inorganic film, which may be hydrophobic or of metal lead to the formation of a polar Langmuir-Blodgett multilayer film. This property is general and holds also for amphiphilic molecules bearing chromophores of different chemical structures, such as merocyanine, p-nitroaniline, p-nitrocinnamic acid, etc. Multilayers consisting of two or more monolayers were prepared and shown to be stable by contact angle measurements and by infra-red or ultraviolet spectroscopies. These facts show that any group may be attached to the terminal carbon of the chain without interferring with the ability of the molecule to form a stable, polar, Z-type multilayer.

The following examples are illustrative of this invention but are not to be interpreted in a limiting sense.

The compounds described in this invention have been prepared by conventional synthetic methods. The compounds are novel and they have been identified by conventional chemical and physical methods. Similar molecules bearing ester groups instead of the amide groups have been synthesized as well, and all of them have been demonstrated to form under identical conditions, the normal type Y-multilayers which do not display pyroelectricity, piezoelectricity or second harmonic generation.

EXPERIMENTAL

Commerical reagents and solvents were purchased from standard chemical suppliers. The reaction of succinimidyl esters with lysine was carried out by the method of A. Paquet, Can. J. Chem. 54, 733 (1976). IR-Spectra were run on a Nicolet MX-1 FTIR spectrometer and 1H-NMR spectra on a Varian FT-80A (80 MHZ) spectrometer; chemical shifts are given in δ, relative to tetramethylsilane, and for multiplets (m) or broad signals they are given in a range or at the center. Mass spectra recorded on a Varian MAT 731 and melting points were taken on a Buchi apparatus according Tottoli and are uncorrected.

EXAMPLE 1

N-(1 Oxohexadecyl)-6-aminohexanoic acid

A mixture of 1.89 g (6.88 mmol) hexadecanoylchloride, 2.00 g (15.24 mmol) 6-aminohexanoic acid, 25 ml dioxane, 25 ml water and 5 ml pyridine is stirred for 4 h at 25° C. The white precipitate is removed by filtration, washed with methanol and recrystallized twice from methanol to yield 0.91 g (36%) of colourless crystals, m.p. 107–109° C. IR (KBr): 3316, 2954, 2917, 2850, 1696, 1636, 1547, 1472, 1425 cm$^{-1}$; $^1$H−NMR (CDCl$_3$): δ=0.86 (br. t, 3H), 1.26 (m, 32H), 2.19 (m, 4H), 3.24 (m, 2H), 517 (br. signal, 1H); MS (70 eV): m/e>369 (13%, M1), 173 (basepeak). 50–200 μl of a 1.5×10$^{-4}$-9.5×10$^{-4}$ M solution of this material in chloroform and trifluoracetic acid (ca.100:1) spread at temperature of 20° C. onto a water surface between two teflon barriers of a monolayer trough (Fromherz designs Fa. Mayer, Gothingen, FRG). By moving one barrier against the other, a surface pressure of 0.46 or 0.048 N/m, recorded by a Wilhelmi balance, was obtained and kept automatically constant. Through this monolayer a hydrophilic glass slide (1.1×3.0 cm) was passed out and in repeatedly starting either from inside or outside the subphase, at a dipping rate of 2 cm/min and a dipping length (length of the glass side which moves into the water) of 2.0 cm. Transfer was observed only when the glass slide was moved through the monolayer outside of the subphase (Z-type) and a polar film of 4 layers was built up.

EXAMPLE 2

N-(1-Oxohexadecyl)-12-aminododecanoic acid

A sample of 5.13 g (20.0 mmol) hexadecanoic acid, 2.30 g (20.0 mmol) N-hydroxysuccinimide and 4.53 g (22.0 mmol) dicyclohexylcarbodiimide (DOC) was dissolved in 20 ml dry tetrahydrofurane or methylenechloride. The temperature of the reaction mixture was kept at 20° C. and the mixture stirred overnight under an atmosphere of nitrogen. The precipitate was removed by filtration and the filtrate concentrated by rotoevaporation to dryness to yield 6.0 g (85%) of the succinimidylester. 180 mg (0.509 mmol) of this active ester and 110 mg (0.510 mmol) 12-aminododecanoic acid were suspended in 3 ml dry dimethoxyethane or dioxane and stirred at 50°–60° C. for ca. 4 h. The reaction mixture was filtered hot and diluted with ice water. The precipitate was removed by filtration and purified by crystallization from methanol to yield 165 mg (72%) of the product as colourless cystals, m.p. 119°–121° C.

IR(KBr): 3317, 2954, 2919, 2850, 1696, 1635, 1545, 1535, 1472, 1270 cm$^{-1}$;

$^1$H-NMR(CDCl$_3$; CF$_3$COOD); δ0.87 (br. 7, 3H), 1.25 (m, 44H), 2.38 (m, 4H), 3.31 (br.t, 2H); MS (70 eV): m/e=453 (M+).

A monolayer of this material on water was transferred to a glass slide as described for example 1 at T=20° C. and surface pressures of 0.020, 0.025 and 0.030 N/m to give a polar film of 6 layers (Z type).

EXAMPLE 3

N-(1-Oxoundecyl)-12-aminododecanoic acid

Reaction similar to example 2, of 9.30 g (50.0 mmol) N-hydroxysuccinimide and 12.0 g (58.0 mmol) DCC gave 14.0 g (100%) of the succinimidylester, which was reacted with 12.5 g (58.1 mmol) 12-aminododecanoic acid to yield 12.3 g (65%) colourless crystals, m.p. 102°–104° C. (methanol).

IR(KBr):3318, 2954, 2919, 2850, 1696, 1635, 1544, 1472 cm$^{-1}$; $^1$H-NMR(CDCl$_3$); δ=0.87 (br. t, 3H), 1.26(m,23.H), 2.20(m,4H), 3.19(m.2H), 5.6 (br. signal, 1H); MS(70 eV): m/e=383(13%, M+), 198 (basepeak). C$_{23}$H$_{45}$NO$_3$ (383.6): Calcd C,72.01 H, 11.83 N,3.65; Found C,71.93 H,11.61 N, 3.94.

As in example 1, a monolayer of this material on water was transferred to glass slides at temperatures of 17° C. and 25° C. and surface pressures of 0.015, 0.020 and 0.030 N/m to give polar films of 5 layers (Z-type).

EXAMPLE 4

N-(1-Oxo-11-bromoundecyl)-12-aminododecanoic acid

Similar to example 2, reaction of 5.30 g (20 mmol) of 11-bromoundecanoic acid with 2.3 g (20 mmol) N-hydroxysuccinimide and 4.12 g (20 mmol) DCC gave 5.6 g (77%) of the succinimidylester. 3.60 g (10 mmol) of this material was reacted with 2.10 g (9.7 mmol) 12-aminododecanoic acid to yield 2.45 g (5.4%) colourless crystals, m.p. 122° C. (methanol).

IR(KBr): 3313, 2920, 2879, 2852, 1696, 1634, 1536, 1472, 1414, 1228 cm$^{-1}$; 1H-NMR(CDCl$_3$): δ1.28(m, 34H), 2.25(m, 4H), 3.23(m, 2H), 3.40(t,2H), 5.3 (br. signal, 1H); MS(70 eV): m/e=463(7.3%, M$^+$+1), 461(7.4%, M+−1), 198 (basepeak). C$_{23}$ H$_{44}$ Br NO$_3$ (462.5): Calcd. C,59.73 H, 9.59 N, 3.03. Found C,60.07 H, 9.64 N, 3.28.

As in example 1, a monolayer of this material on water was transferred to glass slides at 20° C. and 0.020 and 0.025 N/m to give polar films of 5 layers (Z-type).

EXAMPLE 5

N-(1-Oxo-11-iodoundecyl)-12-aminododecanoic acid

Similar to example 2, reaction of 07.90 g (25.3 mmol) 11-iodoundecanoic acid with 2.90 g (25.3 mmol) N-hydroxysuccinimide and 5.22 g (25.3 mmol) DCC gave 10.0 g (96%) of the succiminidylester, which was reacted with 5.40 g (25.1 mmol) 12-aminododecanoic acid to yield 10.5 g (84%) of colourless crystals, m.p. 107°–110° C. (methanol).

IR(KBr): 3310, 2920, 2850, 1695, 1635, 1525 cm$^{-1}$;

$^1$H-NMR(CDCL$_3$): δ=1.28(m, 34H), 2.17(m, 4H), 3.18 (br. t, 4H), (br. signal, 1H); MS(70 eV); m/e=509 (5%, M+), 198 (basepeak).

Following example 1, transfer to glass slides was carried out at 20° C. and 0.020 or 0.25 N/m to give polar films of 5 layers (Z-type).

EXAMPLE 6

(E)-N-(1-Oxo-12-phenyl-11-dodecenyl)-12-aminododecanoic acid

Similar to example 2, reaction of 800 mg (2.92 mmol) (E)-12-pheyl-11-dodecenoic acid with 335 mg (2.91 mmol) N-hydroxysuccinimide and 630 mg (3.05 mmol) DCC gave 600 mg (60%) of the corresponding succinimidylester, which was reacted with 350 mg (1.63 mmol) 12-aminododecanoic acid to yield 560 mg (73%) of colourless crystals, m.p. 119°–121° C. (methanol).

IR(KBr): 3318, 2929, 2881, 2851, 1696, 1634, 1534, 1472, 1216, 964 cm$^{-1}$;

1H-NMR(CDCl$_3$): δ=1.1–2.1(m, 32H), 2.20(m, 6H), 3.22(m, 2H), 5.1 (br signal, 1H), 6.32(m, 2H), 7.29(m, 5H). MS(70 eV)m/e=471(M+).

Following example 1, transfer to glass slides was carried out at 20° C. and 0.025 N/m to give polar films of 6 layers (Z-type).

EXAMPLE 7

N-[N-(4-Nitrophenyl)-1-oxo-12-aminododecyl-12-aminododecanoic acid

Similarly to example 2, reaction of 4.00 g (11.9 mmol) N-(4-nitrophenyl)-12-aminododecanic acid with 2.10 g (18.2 mmol) N-hydroxysuccinimide and 3.70 g (17.9 mmol) DCC gave 5.10 g (99%) of a yellow material, which contained several components according to TLC analysis. Column chromatography on 300 g silica gel (70-230 mesh ASTM) with methylene chloride as eluent gave 1.35 g (45%) of the corresponding succinimidylester. This was reacted with 0.700 g (3.25 mmol) 12-aminododecanoic acid to yield 980 mg (59%) of a yellow powder, m.p. 135°–136° C. (methanol).

IR(KBr): 3371, 3323, 2920, 2851, 1640, 1604, 1534, 1469, 1321, 1307, 1278, 1115 cm$^{-1}$;

1H-NMR(CDCl$_3$, Me$_2$SOOd$_6$): $\delta$=1.27 (m, 36H), 2.16(m, 4H), 3.17(m, 4H), 5.8 (br. signal, 1H), 6.5 (br. signal, 1H), pseudo AB($\delta_A$=6.54, $\delta_B$=8.02, J=9.4 Hz, 4H).

MS(70 eV):M/e=536(10%, M$^+$+2), 162 (basepeak).

C$_{30}$H$_{51}$,N$_3$,O$_5$(533.7): Calcd. C, 67.51 H, 9.63 N, 7.87; Found C, 67.50 H, 9.68 N, 8.12.

As in example 1, a monolayer from this material was formed from a solution in chloroform/methanol (ca.4:1) and transfer to glass slides was carried out at 25° C. and 0.20 N/m to give polar films of 5 layers (Z-type).

EXAMPLE 8

N-[N-4-Nitropheyl)-1-oxo-12-aminododecyl-6-aminohexanoic acid

As in example 7, 1.13 g (2.61 mmol) of the succinimidyl ester of N-(4-nitropheyl)-12 aminododecanoic acid was reacted with 1.18 g (8.95 mmol) 6-aminohexanoic acid to give 0.5 g (43%) of yellow crystals; m.p. 95°–96° C. Transfer to glass slides was carried out at 25° C. and 0.015 N/m to give polar films of 10 layers (Z-type).

EXAMPLE 9

1-[11-(11-Potassiumcarboxylato-undecylamino)-11-oxoundecyl-4-[(4-oxocyclohexadienylidene ethylidene-1,4-dihydropyridine (9)

A solution of 0.32 g (3.44 mmol)-picoline and 1.70 g (3.36 mmol) carboxylic acid obtained in example 5 in 10 ml iso-propanol was refluxed for 16 h. After cooling, the precipitate was collected by filtration and crystallized from ethanol to yield 1.6 g (79%) of colourless crystals. A solution of these crystals, 0.410 g (3.36 mmol) 4-hydroxybenzaldehyde and 0.3 ml piperidine was refluxed in 20 ml ethanol for 17 h. After cooling the red precipitate was filtered, suspended in 45 ml aqueous 0.2M KOH and stirred at 50°–60° C. for 30 min. The resulting crystals were isolated by filtration, dissolved in hot methanol and crtystallized again by adding water to yield 950 mg (58%) of red crystals, m.p. 225°–235° C. For spectral analysis the material was crystallized again from methanol only and dried in the vacuum dessiccator over phosphorus pentoxide, which was, however, not sufficient to take out the water completely.

IR(KBr): 3312, 2919, 2851, 1643, 1623, 1601, 1558, 1521, 1470, 1286, 1171, cm$^{-1}$.

1H-NMR (Me$_2$SO, d$_6$): 1.1–2.1(m, 34H), 2.15 (br. t, 4H), 3.14(br. t, 2H), 4.48(br. t, 2H), pseudo AB(-$\delta_A$=6.85,$\delta_B$=7.60, J=8.6 Hz, 4H), AB($\delta_A$=7.18, $\delta_B$=7.85, J=16.3 Hz, 2H), pseudo AB($\delta_A$=8.05, $\delta_B$=8.69, J=6.9 Hz, 4H).

As in example 7, transfer to glass slides was carried out at 20° or 25° C. and 0.017 N/m to give polar films of 16 layers (Z-type).

EXAMPLE 10

1-[11[12-pentylamino)-12oxododecylamino-11-oxoundecylamino-4-[(4-oxocylclohexadienylidene)ethylidene 1,4-dihyropyridine A mixture of 760 mg (1.43 mmol of the N$^{13}$(1-oxo-11-bromoundecyl)-1-(pentylamino)-1-oxo-12-aminododecane 190 mg (2.04 mmol)-picoline was stirred at 140° C. for 4 h. The resulting black oil was dissolved in little ethanol: By adding boiling acetone and cooling the solution 440 mg (49%) of violet crystals were obtained. A solution of 110 mg (0.900 mmol) of these crystals and 0.1 ml piperidine in 10 mol ethanol was refluxed for 16 h. After cooling, dark red crystals were obtained, which were suspended in 8 ml aqueous 0.2M KOH and stirred at 50°–60° C. for 40 min. The dark red-blue material was collected by filtration, washed with water and acetone and dried in the vacuum desiccator over phosphorous pentoxide to yield 380 mg (38%) of dark blue crystals, which start to melt at 115° C. The product is further purified by column chromatography on 10 g neutral aluminium oxide with methanol/conc. aq. ammonia (100:1) and final crystallization from methanol/acetone.

IR(KBr): 3307, 2921, 2851, 1640, 1559, 1504, 1468, 1441, 1320, 1147 cm$^{-1}$

1HNMR (CD$_3$OD): $\delta$=0.90 (br. t, 3H), 1.29 (m, 40H), 2.10 (m, 4H), 3.14 (br. t, 4H), 4.32(m, 2H), pseudo AB($\delta_A$=6.60, $\delta_B$=7.42, J=8.7 Hz, 4H) AB($\delta_A$=6.85, $\delta_B$=7.75, J=15.8 Hz, 2H), pseudo AB ($\delta_A$=7.79, $\delta_B$=8.39, J=6.7 Hz, 4H); MS(70 eV):m/e=349(6%, M$^+$+1), 138 (basepeak).

As in example 7, transfer to glass slides was carried out at 20° or 25° C. and 0.017 N/m to give polar films of 16 layers (Z-type).

EXAMPLE 11

N-(1-Oxoundecyl)-12-aminodecanoic amide

As in example 2, reaction of 5.00 g (13 mmol) of the acid obtained in example 3 with 1.50 g (13 mmol) N-hydroxysuccinimide and 2.68 g (13.0 mmol) DCC gave 4.2 g (67%) of the corresponding succiminidyl ester. 500 mg (1.04 mmol) of this material was suspended in 3 ml 25% aqueous ammonia solution and stirred for 18 h. Filtration yielded a colourless solid, which was crystallized three times from ethanol to give 180 mg (47%) colourless crystals, m.p. 140°–142° C.

IR(KBr): 3401, 332, 3198, 2920, 2851, 1646, 1637, 1532, 1472, 1422 cm$^{-1}$;

1H-NMR(CDCl$_3$): $\delta$=0.87 (br. t, 3H), 1.26 (m, 34H), 2.17(m, 4H), 3.20(m, 2H), 5.5 (br. signal, 1H), 5.9 (br. signal, 2H); MS(70 ev: m/e=383 (7%, M$^+$=1), 324 (basepeak).

C$_{23}$H$_{46}$N$_2$O$_2$(382.6): Calcd. C, 72.20 H, 12.12 N, 7.32; Found C, 71.97 H, 12.12 N, 7.29.

As in example 1, a monolayer from this material spread from a chloroform solution and transfer to glass slides at 20° C. and 0.019 N/m gave polar films. (7 Z-type layers).

EXAMPLE 12

N$^6$-(1-Oxohexadecyl)-L-Lysine

Following the procedure of A. Paquet Can. J. Chem. 54, 733 (1976), 353 mg. (1 mmol) of the succinimidylester of hexadecanoic acid, prepared as in example 2, was suspended in 2 ml acetone and added to a solution of 183 mg (1 mmol) L-lysine hydrochloride and 0.27 ml (ca. 2 mmol) triethylamine in 2 ml water. The reaction mixture was stirred vigorously for at least 4 h, then neutralized with acetic acid and diluted with water. The precipitate was removed by filtration and washed with water, methanol and ether. Repeated crystallizations from acetic acid/water and acetic acid gave 280 mg (73%) colourless crystals, m.p. 240°–245° C. (reported 210°–220° C.)

IR(KBr): 3328, 2919, 2851, 1639, 1604, 1579, 1559, 1533 1473, 1414 cm$^{-1}$;

1H-NMR (CF$_3$COOD): $\delta$0.89(br. t, 3H), 1.1–2.5(m, 32H), 2.75, (m, 2H), 3.65(m,2H), 4.42(m, 1H):

$C_{22}H_{44}N_2O_3$ (384.6): Calcd. C, 68.70 H, 11.53; Found C, 68.71 H, 11.63.

Following example 1, transfer was carried out at 20° C. and 0.20 or 0.025 N/m to give polar films of 6 layers (Z-type).

EXAMPLE 13

$N^6$-[1-Oxoundecyl)-1-oxo-12-aminododecyl-L-Lysine

As in example 2, reaction of 5.00 g (13.0 mmol) of the acid, prepared as in example 3, with 1.50 g (13.0 mmol) N-hydroxysuccinimide and 2.68 g (13.0 mmol) DCC gave 4.2 g (67%) of the corresponding succinimidylester.

As in example 12, 240 mg (0.5 mmol) of this material yielded 115 mg (45%) of colourless crystals, m.p. 245°-250° C. (from acetic acid).

IR(KBr): 3333, 2920, 2851, 1638, 1609, 1583, 1474, 1413, 1328 cm$^{-1}$, $^1$H-NMR(CF$_3$COOD): δ=0.89 (br. t, 3H), 1.1–2.6 (m, 40H), 2.76 (m, 4H), 3.60 (m, 4H), 4.40 (m, 1H);

$C_{29}H_{57}N_3O_4$ (511.8): Calcd. C, 68.05 H, 11.23 N, 8.21; Found C, 68.16 H, 10.95 N, 7.77.

Following example 1, transfer to glass slides was carried out at 20° C. and 0.020 or 0.025 N/m to give polar films of 8 layers (Z type).

EXAMPLE 14

$N^6$-[1-Oxo-12-(decylcarbonyloxy) dodecyl-L-lysine

As in example 2, reaction of 1.00 g (2.60 mmol) 12-decylcarbonyloxy)-dodecanoic acid with 420 mg (3.28 mmol) N-hydroxysuccinimide and 580 mg (2.80 mmol) DCC gave 1.30 g of a colourless solid, which was extracted by ca. 50 ml hot carbon tetrachloride. Evaporation of the solvent yielded 790 mg (63%) of the corresponding succinimidyl ester. As in example 12, from 480 mg (0.997 mmol) of this material was obtained 110 mg (22%) of the amino acid as colourless crystals, m.p. 232°-236° C. from acetic acid).

IR(KBr): 3328, 2919, 2852, 1736, 1640, 1581, 1531, 1471, 1179 cm$^{-1}$;

$C_{29}H_{56}N_2O_5$ (512.7): Calcd. C, 67.93 H, 11.01 N, 5.46; Found C, 68.20 H, 10.84 N, 5.27.

Following example 1, transfer to glass slides was carried out at 20° C. and 0.020 N/m to give polar films of 5 layers (Z-type).

EXAMPLE 15

$N^6$-[N-(1-oxo-11-bromoundecyl)-1-oxo-12-aminododecyl-L-lysine

As in example 2, reaction of 240 g (5.19 mmol) of the acid, prepared as in example 4, with 0.62 g (5.39 mmol) N-hydroxysuccinimide and 1.12 g (5.43 mmol) DCC gave 2.50 g (86%) of the corresponding succinimidylester.

As in example 12, from 280 mg (0.500 mmol) of this material was obtained 130 mg (44%) of the amino acid as colourless crystals, m.p. 225°-227° C. from acetic acid.

IR(KBr): 3327, 2919, 2851, 1637, 1607, 1582, 1529, 1474, 1413, 1328 cm$^{-1}$;

1H-NMR (CF$_3$COOD): δ=1.1–2.6 (m, 40H), (m, 40H), 2.80 (m, 4H), 3.5 (m, 6H), 4.45 (m, 1H).

$C_{29}H_{56}BrN_{34}$ (590.7): Calcd. C, 58.96 H, 9.56 N, 7.11; Found C, 59.27 H, 9.50 N, 6.71.

Following example 1, transfer to glass slides was carried out at 20° C. and 0.019 N/m to give polar films of 5 layers (Z-type).

EXAMPLE 16

$N^6$-[N-1-oxo-11-iodoundecyl-1-oxo-12-aminododecyl]-L-lysine

As in example 2, reaction of 6.00 g (11.8 mmol) of the acid prepared as in example 5, with 1.50 g (13.0 mmol) N-hydroxysuccinimide and 2.70 g (13.1 mmol) DCC gave a colourless solid, which was crystallized from carbontetrachloride to yield 2.6 g (35%) of the corresponding succinimidylester. As in example 12, from 303 mg (0.500 mmol) of this material 110 mg (35%) of the amino acid were obtained as colourless crystals, m.p. 220°-222° C. (acetic acid).

IR (KBr): 3308, 2919, 2850, 1641, 1609, 1584, 1540, 1470, 1416 cm$^{-1}$;

$C_{29}H_{56}IN_3O_4$ (637,7): Calcd. C, 54.62 H, 8.85 N, 6.59; Found C, 54.47 H, 8.80, N, 6.13.

As in example 1, transfer to glass slides was carried out at 20° C. and 0.025 N/m to give polar films of 4 layers (Z type).

EXAMPLE 17

(E)-$N^6$-(N-1-Oxo-12-phenyl-11-dodecenyl)-1-oxo-12-aminodocecyl L-lysine

As in example 2, reaction of 515 mg (1.09 mmol) of the acid, prepared as in example 6, with 150 mg (1.30 mmol) N-hydroxysuccinimide and 270 mg (1.30 mmol) DCC gave 340 mg (56%) of the corresponding succinimidylester. As in example 12, from 280 mg (0.492 mmol) of this material 160 mg (54%) of the amino-acid were obtained as colourless crystals, m.p. 230° C. from acetic acid/water.

IR(KBr): 3311, 2919, 2851, 1638, 1585, 1539, 1470, 1448, 1418, 964 cm$^{-1}$;

$C_{36}H_{61}N_3O_4$ (602.9): Calcd. C, 71.71 H, 10.20 N, 6.97; Found C, 71.80 H, 9.98 N, 6.42

As in example 1, transfer to glass slides was carried out at 20° C. and 0.015 N/m to give polar films of 4 layers (Z-type).

EXAMPLE 18

$N^6$-[N-[N-(4-nitrophenyl)-1-oxo-12-aminododecyl-1-oxo-12-aminododecyl[-L-lysine As in example 2, reaction of 800 mg (1.50 mmol) of the acid, prepared as in example 7, with 200 mg (1.74 mmol) N-hydroxysuccinimide and 360 mg (1.75 mmol) DCC gave 530 mg (56%) of the corresponding succinimidylester. As in example 12, from 200 mg (0.317 mmol) of this material 45 mg (21%) of the amino acid were obtained after repeated recrystallizations from acetic acid/water as a yellow solid, m.p. 236°-239° C.

IR(KBr): 3318, 2926, 2851, 1640, 1603, 1534, 1507, 1472, 1322, 1305, 1111 cm$^{-1}$;

$C_{36}H_{63}N_5O_6$ (661.9): Calcd. C, 65.32 H, 9.59 N, 10.58; Found C, 65.02 H, 9.70 N, 10.32.

As in example 7, transfer to slides, covered with octadecyltrichlorosilane, and hydrophilic glass slides was carried out at 25° C. and 0.021 N/m to give polar films of 20 layers (Z-type).

EXAMPLE 19

N⁶-[N-(4-Nitrophenyl)-1-oxo-12-aminododecyl -1-oxo-6-aminohexyl -L-lysine (19)

As in example 12, from 531 mg (1.00 mmol) of the succinimidylester of the acid, prepared in example 8, were obtained 90 mg of the amino acid as yellow crystals, m.p. 305°–220° C. from acetic acid/water. (not yet clean)

EXAMPLE 20

(E)-N⁶-[N-[1-Oxo-3-(4-nitrophenyl)-2-Propenyl -12-aminododecyl -L-lysine

As in example 12, from 900 mg (1.85 mmol) of the succinimidylester of N-[1-oxo-3-(4-nitropheyl)-2-propenyl -12-aminododecanoic acid were obtained 80 mg of the amino acid as colourless crystals, m.p. from acetic acid.

As in example 1, transfer to glass slides was carried out at 20° C. and 0.019 N/M to give polar films of 5 layers (Z-type).

IR(KBr): 3303, 2931, 2921, 2850, 1719, 1700, 1652, 1617, 1541, 1523, 1471, 1346, 1217, Cm⁻¹

H-NMR (CF₃COOD): δ1.3–1.8 (m, 24H), 3.2–4.0 (m, 6H) 6.8(d, 1H), 7.6 (d, 1H), 7.74 (d, 2H), 8.21 (d,2H).

We claim:

1. Amphiphilic molecules suited for the production of Z-type Langmuir-Blodgett multilayer films of the formula:

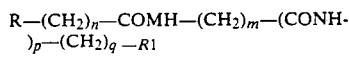

where R designates —CH₃, —CH₂Hal, —CH=CH—φ, —NH—=—NO₂, or

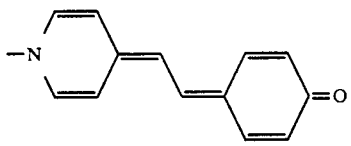

where R₁ designates —CH, —OOOH, —NH₂, —OONH₂, —PO₃=,

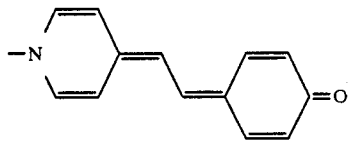

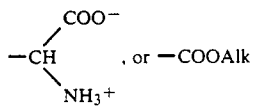, or —COOAlk wherein at least one of R and R₁ is

where Hal designates a halogen atom, Alk designates an alkali metal atom and where the sum of n,m and q is 14 and p is zero or one and where there may be more than 2 alkyl-amido entities.

* * * * *